US00PP29820P3

(12) United States Plant Patent
Clark et al.

(10) Patent No.: US PP29,820 P3
(45) Date of Patent: Nov. 6, 2018

(54) COLEUS PLANT NAMED 'UF14-24-1'

(50) Latin Name: *Plectranthus scutellarioides*
Varietal Denomination: UF14-24-1

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 8 days.

(21) Appl. No.: 15/530,980

(22) Filed: Mar. 31, 2017

(65) Prior Publication Data

US 2018/0288928 P1 Oct. 4, 2018

(51) Int. Cl.
*A01H 5/12* (2018.01)

(52) U.S. Cl.
USPC ..... Plt./469
CPC ..... *A01H 5/12* (2013.01)

(58) Field of Classification Search
USPC ..... Plt./469, 373
CPC ..... A01H 5/12; A01H 5/00
See application file for complete search history.

(56) References Cited

U.S. PATENT DOCUMENTS

PP21,585 P2 12/2010 Clark et al.
PP23,585 P3 5/2013 Clark et al.
PP25,626 P3 6/2015 Clark et al.
PP25,627 P3 6/2015 Clark et al.
PP25,650 P3 6/2015 Clark et al.
PP25,651 P3 6/2015 Clark et al.
PP25,652 P3 6/2015 Clark et al.
PP25,653 P3 6/2015 Clark et al.
PP27,076 P3 8/2016 Clark et al.
PP27,077 P3 8/2016 Clark et al.
PP27,078 P3 8/2016 Clark et al.
PP27,126 P3 8/2016 Clark et al.
PP27,140 P3 9/2016 Clark et al.
PP27,269 P3 10/2016 Clark et al.
PP27,288 P3 10/2016 Clark et al.
PP27,499 P2 12/2016 Clark et al.
PP27,500 P2 12/2016 Clark et al.

OTHER PUBLICATIONS

U.S. Appl. No. 13/986,163, filed Apr. 5, 2013, Clark et al.
U.S. Appl. No. 14/999,961, filed Jul. 19, 2016, Clark et al.
U.S. Appl. No. 14/999,962, filed Jul. 19, 2016, Clark et al.
U.S. Appl. No. 14/999,963, filed Jul. 19, 2016, Clark et al.
Deng et al., "Ornamentals," University of Florida, Apr. 2013; 3 pages.
Nguyen et al., "Genetics of growth habit and development of new coleus (*Solenostemon scutellarioides* (L.) Codd) varieties with trailing habit and bright color," *J Hered,* 99:573-580; 2008.

*Primary Examiner* — Kent L Bell
(74) *Attorney, Agent, or Firm* — Dentons US LLP

(57) ABSTRACT

'UF14-24-1' is a new coleus plant distinguished by having a vigorous compact mounded growth habit, excellent heat tolerance, consistent bright chartreuse leaves when grown in both sun and shade conditions, and desirable late flowering characteristics, as disclosed herein.

3 Drawing Sheets

Latin name of the genus and species of the plant claimed: *Plectranthus scutellarioides.*

Cultivar denomination: 'UF14-24-1'.

BACKGROUND OF THE INVENTION

The invention relates to a new and distinct cultivar of coleus plant named 'UF14-24-1'. 'UF14-24-1' originated from an open pollination conducted in May-November 2012 in Gainesville, Fla. between the female coleus plant 'UF13-1-6' (unpatented) and an unknown male coleus plant. A single seedling was chosen in May 2014 for further asexual propagation in Gainesville, Fla.

'UF14-24-1' has been reproduced asexually for over two years through vegetative cuttings and has been found to retain its distinctive characteristics through successive asexual propagations. 'UF14-24-1' was first propagated asexually by meristem tip cuttings in May 2014 in Gainesville, Fla., and has remained true-to-type since that time.

'UF14-24-1' has not been made publicly available more than one year prior to the filing date of this application.

When compared to the female parent 'UF13-1-6', 'UF14-24-1' has chartreuse ovate to lance-shaped leaves that are much longer than wide, while 'UF13-1-6' has much larger leaves colored lemon yellow with purple margins. 'UF14-24-1' has an extremely vigorous well-branched mounded habit, whereas 'UF13-1-6' is vigorous, but much more upright in habit and less lateral branching.

'UF14-24-1' has bright chartreuse foliage color similar to 'UF08-4-3' (U.S. Plant Pat. No. 23,585); however, 'UF14-24-1' is not as upright and rangy in growth habit as is 'UF08-4-3'. 'UF14-24-1' has lance-shaped leaves and a mounded growth habit similar to 'UF12-82-3' (U.S. Plant Pat. No. 27,288) and 'UF12-73-5' (U.S. Plant Pat. No. 27,499); however, the foliage color of 'UF12-82-3' and 'UF12-73-5' is not purely chartreuse as is the foliage color of 'UF14-24-1'.

SUMMARY OF THE INVENTION

The following are the most outstanding and distinguishing characteristics of 'UF14-24-1' when grown under normal horticultural practices in Gainesville, Fla. 'UF14-24-1' has a combination of a novel, vigorous, compact upright growth habit, excellent heat tolerance, and consistent bright chartreuse leaves. 'UF14-24-1' has superior foliage color stability in both sun and shade conditions, maintaining stable color in all conditions. 'UF14-24-1' has a vigorous but compact upright growth habit with excellent lateral branching when grown as a stock plant, thus providing ample vegetative propagules for producers. Due to the plant never being observed to produce flowers in Gainesville, Fla., 'UF14-24-1' is desirable for long-season performance in the landscape.

BRIEF DESCRIPTION OF THE DRAWINGS

This new coleus plant is illustrated by the accompanying photographs, which show the plant's form and foliage. The colors shown are as true as can be reasonably obtained by conventional photographic procedures.

FIG. 2—shows the growth habit, form, and foliage of the claimed plant.

FIG. 3—shows a close-up of the foliage of the claimed plant.

DETAILED BOTANICAL DESCRIPTION

Figure 1:
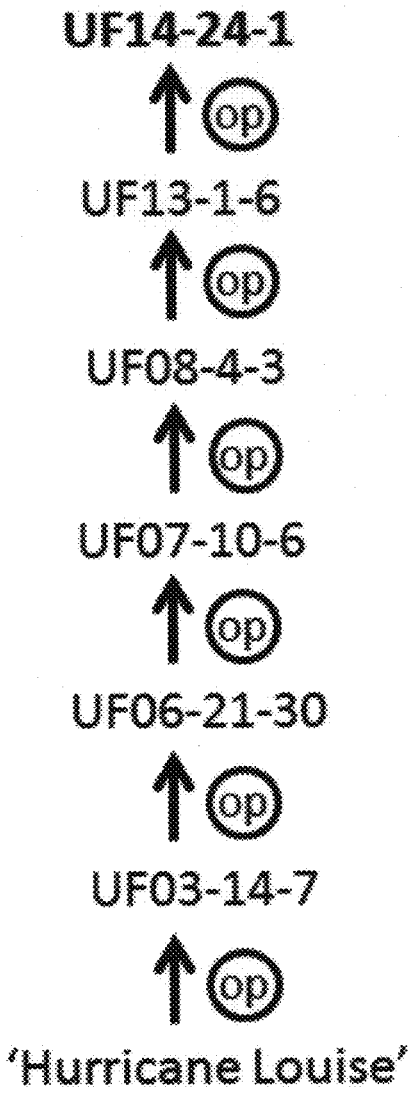
FIG. 1—shows the pedigree of the claimed plant.
Figure 2:
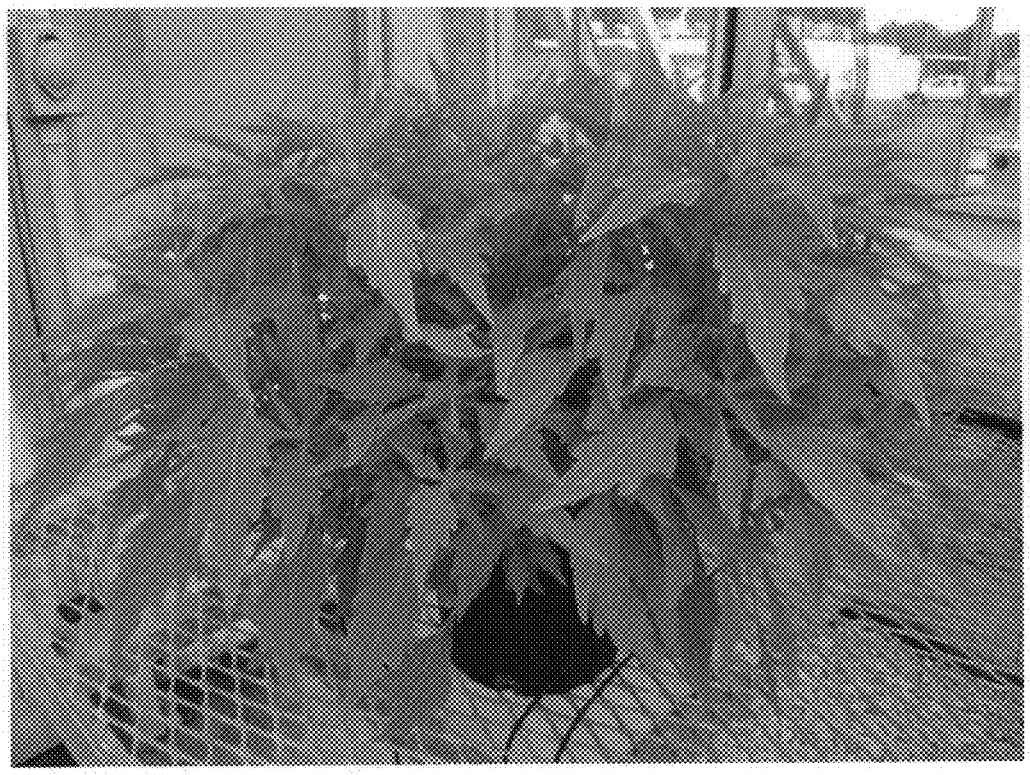
FIGS. 2 and 3 were taken of plants grown for eleven weeks from unrooted cuttings in October-December, 2016 in a poly-covered plastic greenhouse in Gainesville, Fla.
Figure 3:
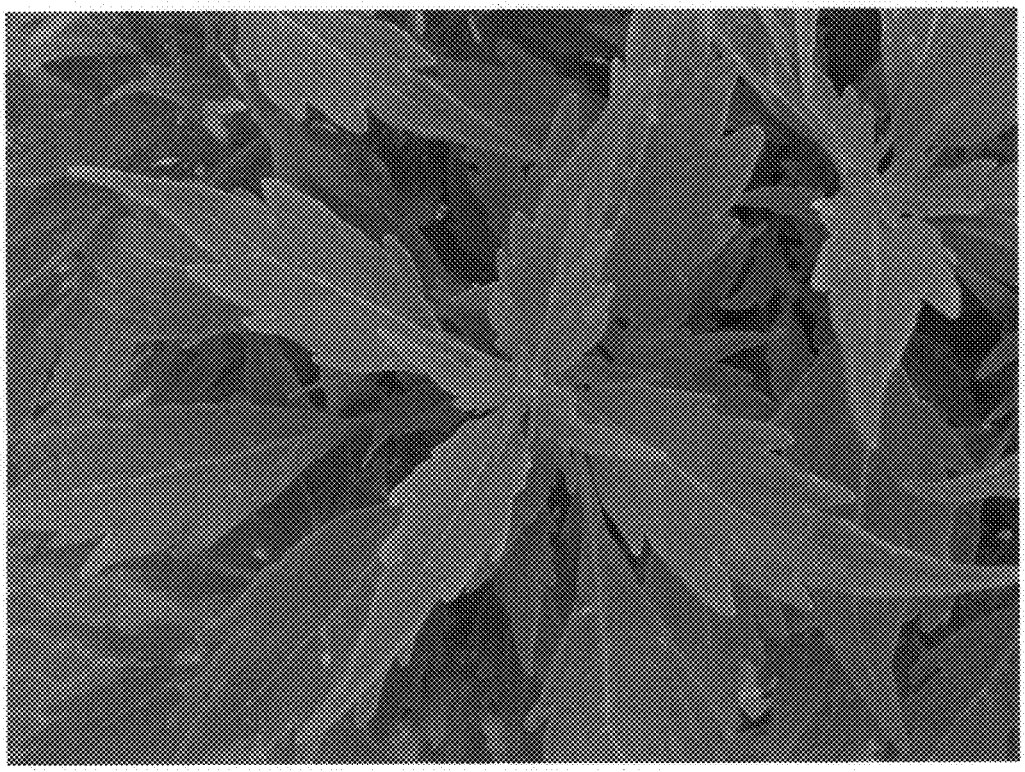

The following detailed description sets forth the distinctive characteristics of 'UF14-24-1'. The detailed description was obtained using eleven-week-old plants grown from unrooted cuttings in October-December of 2016 in a poly-covered plastic greenhouse in Gainesville, Fla. The plants were propagated in mist for 10 days after cuttings were stuck, then grown in 1-gallon pots for approximately nine and a half additional weeks. Color references are to The R.H.S. Colour Chart of The Royal Horticultural Society of London (R.H.S.), 2007 5th Edition.

Classification:

*Family*.—Lamiaceae.

*Botanical*.—*Plectranthus scutellarioides*.

*Common name*.—Coleus.

*Cultivar name*.—'UF14-24-1'.

Plant description:

*Form*.—Spreading.

*Habit*.—Loosely Mounded.

*Height* (*from top of soil*).—25-30 cm.

*Width* (*horizontal plant diameter*).—60-65 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—12-14.

*Branch color*.—RHS 144B.

*Texture*.—Smooth.

*Pubescence*.—Not present.

*Stem description*.—Square-shaped stem, 0.8 cm in diameter at the soil line.

*Branch diameter*.—0.5-0.6 cm at the base of a 24 cm long branch.

*Branch length*.—22-25 cm.

*Internode length*.—4-5 cm.

*Anthocyanin*.—Not present.

Leaves:

*Quantity of leaves per branch*.—18-20.

*Arrangement*.—Opposite.

*Fragrance*.—Not fragrant.

*Shape*.—Ovate to lance-shaped.

*Length*.—10-12 cm.

*Width*.—3-4 cm.

*Apex*.—Narrowly acute.

*Base*.—Oblique.

*Margin*.—Lobed.

*Leaf texture* (*both surfaces*).—Smooth.

*Pubescence color* (*both surfaces*).—Not present.

*Venation color*.—Upper surface: Center: RHS 4D. Lower surface: RHS 145C.

*Venation pattern*.—Upper surface: Arcuate. Lower surface: Reticulate.

*Color*.—Immature leaf: Upper surface: RHS N144B. Lower surface: RHS 150B.

*Color*.—Mature leaf: Upper surface: RHS N144C. Lower surface: RHS 145A.

*Petiole length*.—4-5 cm.

*Petiole diameter*.—0.2-0.3 cm.

*Petiole color*.—RHS N144D.

*Petiole texture*.—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Pernonspora lamii*) which has been observed in stock materials grown closely together in cooler growing seasons.

What is claimed is:

1. A new and distinct *Plectranthus scutellarioides* plant named 'UF14-24-1' as described and illustrated herein.

* * * * *